United States Patent
Golz-Berner et al.

US006245342B1

(10) Patent No.: US 6,245,342 B1
(45) Date of Patent: Jun. 12, 2001

(54) COSMETIC PREPARATION WITH A PEPTIDE ADDITION

(75) Inventors: Karin Golz-Berner; Leonhard Zastrow, both of Monaco (MC); Nouha Domloge, Roquebrunne-Cap Martin (FR)

(73) Assignee: Lancaster Group GmbH, Mainz (DE)

( * ) Notice: Subject to any disclaimer, the term of this patent is extended or adjusted under 35 U.S.C. 154(b) by 0 days.

(21) Appl. No.: 09/319,091

(22) PCT Filed: Dec. 12, 1997

(86) PCT No.: PCT/DE97/02941

§ 371 Date: May 28, 1999

§ 102(e) Date: May 28, 1999

(87) PCT Pub. No.: WO98/25584

PCT Pub. Date: Jun. 18, 1998

(30) Foreign Application Priority Data

Dec. 12, 1996 (DE) ................................. 196 53 736

(51) Int. Cl.[7] ........................................ A61K 6/00
(52) U.S. Cl. ............... 424/401; 424/401; 424/94.4; 424/60; 424/59; 424/49; 424/400; 424/47; 435/3; 435/259; 435/287; 435/193; 435/420; 435/205; 435/173.7; 435/430; 530/350; 530/403; 530/370; 530/371; 426/574; 426/49; 514/222.5
(58) Field of Search .................... 435/259, 287, 435/205, 173.7, 193, 3, 420, 430; 536/123.1, 123.12; 530/350, 403, 371, 370; 424/49, 400, 47, 401, 60, 59; 426/335, 574, 49; 504/155; 514/222.5

(56) References Cited

U.S. PATENT DOCUMENTS

| 5,019,391 | * | 5/1991 | Bunte et al. ................ 424/195.1 |
| 5,202,236 | * | 4/1993 | Maugh et al. ................. 435/69.1 |
| 5,468,474 | * | 11/1995 | Honda et al. .................. 424/70.1 |
| 5,523,090 | * | 6/1996 | Znaiden et al. ................. 424/401 |
| 5,629,185 | | 5/1997 | Stanzl . |
| 5,830,994 | * | 11/1998 | D'Hinterland et al. ............ 530/200 |
| 5,879,688 | * | 3/1999 | Coury et al. ................... 424/401 |
| 5,885,564 | * | 3/1999 | Zastrow et al. ................... 424/74 |
| 5,904,921 | * | 5/1999 | Bresson-Rival et al. ........... 424/94.3 |

FOREIGN PATENT DOCUMENTS 42 41 154    3/1994 (DE) .

OTHER PUBLICATIONS

EP 389,950, Takeuchi et al., Mar. 10, 1990.*

* cited by examiner

Primary Examiner—Karen Cochrane Carlson
Assistant Examiner—Hope A. Robinson
(74) Attorney, Agent, or Firm—Collard & Roe, P.C.

(57) ABSTRACT

A cosmetic preparation contains peptide derivatives from α-MSH, as well as other active components. A cosmetic product has the property of activating the melanogenesis and being an anti-inflammatory and acting more efficiently. The synergetically active preparation also includes a combination of a peptide derivative corresponding to the formula (Lip)X-His-Phe-Arg-Y in a ratio of 0.05 mg to 2.5 mg of a pure peptide derivative per kg of the total mass, while the peptide derivative is mixed with xanthine in a ratio of 0.5 to 2 mol per 100 mol of peptide. Also there is at least 0.5 wt % of a mixture of enzymes and vitamins, containing at least 150 U/ml of superoxide dismutase. Also present are auxiliary agents and carrier agents in a ratio of 65 to 99.5 wt %, and possibly other active components.

10 Claims, 1 Drawing Sheet

COSMETIC PREPARATION WITH A PEPTIDE ADDITION

BACKGROUND OF THE INVENTION

1. Field of the Invention

This invention concerns a new cosmetic preparation containing peptide derivatives derived from α-MSH (melanocyte stimulating hormone) and other active ingredients.

2. The Prior Art

α-MSH has already been investigated by a number of research groups, without so far being able to develop a pharmaceutical drug from it. A specific direction of effect was disclosed in French Patent 2,710,340 A, where certain peptide derivatives derived from α-MSH were described and claimed as active ingredients which stimulate melanogenesis. Topical use against inflammatory reactions of the skin is also described.

SUMMARY OF THE INVENTION

The object of this invention is to develop a new cosmetic preparation especially with melanogenesis-stimulating and anti-inflammatory properties with improved effectiveness.

According to this invention, a cosmetic preparation with a peptide additive consists of a combination of the following active ingredients:

a) a peptide derivative of the formula [Lip]X-His-Phe-Arg-Y, where
  Lip stands for thioctic acid or one of its derivatives,
  X denotes Glu, OH, or $NH_2$,
  Y is Trp-Gly-OH,
    Trp-Gly-$NH_2$,
    Trp-$NH_2$ or
    Trp-OH,
  Phe is homo-Phe or P-fluoro-Phe,
and the amino acids may be in the form D, L or DL, or mixtures thereof, in a ratio of 0.05 to 2.5 mg pure peptide derivative per kg total weight, where the peptide derivative is associated with xanthine in a ratio of 0.5 to 2 mol per 100 mol peptide;

b) at least 0.5 wt % of a mixture of enzymes and vitamins containing at least 150 units/mL (U/mL) peroxide dismutase;

c) the usual excipients and vehicles in the amount of 65 to 99.5 wt %, and d) and additional active ingredients in the amount of 0 to 12 wt %.

The percentage amounts are based on the total weight of the cosmetic preparation in each case.

A lipoyl peptide or peptide mixture known from French Patent No. 2,710,340 A was used as the peptide; it has in particular at least one of the following sequences:

I. [(DL)Lip]-Glu-His-D.HomoPhe-Arg-Trp-Gly-$NH_2$
II. [(DH)Lip]-Glu-His-D.HomoPhe-Arg-Trp-Gly-$NH_2$
III. [(DL)Lip]-Glu-His-parafluoro-Phe-Arg-Trp-Gly-$NH_2$
IV. [(DH)Lip]-His-D.HomoPhe-Arg-Trp-Gly-$NH_2$
V. [N.Lipoyl-lysine]-Glu-His-D.HomoPhe-Arg-Trp-Gly-$NH_2$
VI. [N.Lipoyl-lysine]-His-D.HomoPhe-Arg-Trp-Gly-$NH_2$
VII. [N.Lipoyl-lysine]-His-D.HomoPhe-Arg-Trp-$NH_2$ as well as derivatives of these molecules in the form of salts of the esters or amides, wherein the peptide derivative is mixed with xanthine in a ratio of 0.5 to 2 mol per 100 mol peptide.

In commercial peptides, e.g., MAP® or MAP-X® (from Laboratories Seporga, France), a lipoylaminopeptide of the above peptide derivative, the pure peptide content is about 50 mg/kg, and approximately 0.01 to 5 wt % of this is used in the cosmetic preparation. This yields the above-mentioned peptide content for this invention.

The mixture of enzymes and vitamins used is preferably the digestion product of a yeast prepared by an ultrasonic treatment, with the digestion product containing peroxide dismutase, protease, vitamin $B_2$, vitamin $B_6$, vitamin $B_{12}$, vitamin $D_2$, and vitamin E. It preferably contains at least 150 U/mL peroxide dismutase (POD), protease, and vitamins B and D, with the POD/protease radio in international units being at least in the range of 3:1 to 8:1.

An ultrasonic digestion method, such as that described in German Patent No. 4,241,154 C1 is especially advantageous for preparation of the enzyme/vitamin mixture according to this invention; in this process, a cell dispersion or suspension is passed through an ultrasonic treatment area in an ultrasonic flow-through cell, with the sonotrode extending into the flow-through cell by one-half to two-thirds of its length so that it is submerged in the medium to be treated ultrasonically. The sonotrode here has an angle of 80.5° to 88.5°, and the ratio of the submersion length of the sonotrode in mm to the ultrasonically treated volume in mL is adjusted to a value of 1:1.1 to 1:20. The solids content in the medium to be ultrasonically treated is in the range of 1:0.02 to 1:2.2 (in wt %).

Yeasts, such as baker's yeast, brewer's yeast, wine yeast, as well as specially treated yeasts such as POD-enriched yeasts, for example, can be used as the cell dispersion. A cell dispersion that is advantageous to use may contain *Saccharomyces cerevisiae*, for example.

A particularly advantageous component a) of the cosmetic preparation according to this invention consists of a mixture of the peptide derivative of the following formula, mixed with xanthine:

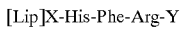

[Lip]X-His-Phe-Arg-Y manufactured with semisynthetic marine peptides and polypeptides which are a bioengineered protein fraction produced from microalgae of the Chlorella genus and with macroalgae of the Ulva genus associated with byssus (silk filament from mollusks) and subsequently associated with a vegetable glucose polymer, and where the semisynthetic marine peptides are associated with 0.5 to 5 wt % marine mineral salts and trace elements.

An example of such a mixture is the product available under the brand name "Sun Marine Complex" (from Laboratories Seproge, Sophia-Antipolis Cedex, France).

This mixture, which is advantageous to use, contains xanthine-associated peptides and semisynthetic marine peptides, the latter associated with glucose polymers, e.g., dextrin, and mineral salts/trace elements from sea water, hereinafter referred to designated SMC (Sun Marine Complex); it is produced by simply mixing the two ingredients together. The semisynthetic marine peptides are produced by enzymatic purification of the tyrosine-rich peptides and polypeptides from byssus, i.e., from the marine mollusks. Then the vegetable cellulose component (microalgae and macroalgae) is treated enzymatically to extract the various mineral and organic elements. Then, under slightly basic conditions and under a relatively high pressure and high temperature, the association with a glucose polymer is induced, e.g., with dextrin to achieve stabilization of the individual elements of the mixture on the gludosidic carrier as a "transport molecule" for the organism.

In SMC the ratio of xanthine-associated peptides is in the range of 0.5 to 10 wt %, preferably 0.5 to 5 wt %. The remainder consists of the semisynthetic marine peptides (associated with dextrin, for example) plus mineral salts and trace elements.

As the conventional additives and vehicles of the topical preparation according to this invention, the following can be used, e.g., isopropyl myristate, isopropyl palmitate, isopropyl stearate, carbomer, cetearyl alcohol, lecithin, copolymers, paraffin oil, cetyl alcohol, propylene glycol, polyglycol, jojoba oil, silicone oil, coconut oil, kaolin modified according to WO 95/17,157, cetyl palmitate, C10–C30 alkyl acrylate cross polymer, magnesium aluminum silicate, hydroxyethylcellulose, as well as other substances suitable for the specific use forms, such as lipstick, eye cosmetics, hair mask products, etc., with which those skilled in the art are familiar.

The preparation may contain as additional active ingredients 1,3- and 1,6-β-glucan, CM-Glucan®, allantoin, $TiO_2$, ZnO and UVA and UVB-blocking substances.

New agglomerates of nonporous spherical $SiO_2$ particles of 0.05–1.5 µm and spherical $TiO_2$ or ZnO particles in which the agglomerates have a particle size of 0.06–5 µm can also be used in the emulsion in the amount of 0.1–30 wt %. Such agglomerates are produced by mixing the particles while stirring at 300–400 rpm and adding some water until achieving a pasty consistency and then adding the remaining water and homogenizing at 3000 to 5000 rpm for 20–60 minutes.

The cosmetic preparation according to this invention surprisingly has a synergistic anti-inflammatory action which goes far beyond the potential of the individual ingredients, and therefore it can be used successfully in cosmetic compositions such as sunscreen emulsions, after-sun emulsions, facial cosmetics, etc., and as cosmetics for other inflammatory dermatological processes. This synergism is demonstrated especially impressively in the fact that an emulsion which contains only 0.5 wt % of the xanthine-associated peptide preparation (with 50 mg peptide per kg) plus the yeast digestion products has the same anti-inflammatory effect as a pure peptide preparation (with 50 mg peptide per kg).

This is shown by measurements on subjects with a Mexameter MX16® (Courage+Khazaka, Germany), using the degree of redness of the skin as the basis for evaluation, with measurements being performed at certain intervals after the radiation exposure. The resulting curves as well as the histological skin tests performed on the volunteers in parallel by the H+E stain method show that with regard to melanocyte activity, that the activity of the preparation according to this invention is far above the activity levels to be expected of the individual ingredients.

A preferred formulation contains the peptide components in a ratio of 0.05 to 1.5 mg pure peptide derivative per kg total weight.

Component a) according to this invention in the combination of xanthine-associated peptides, peptide derivatives and the bioengineered protein fraction of enzyme activators containing semisynthetic marine peptides—the latter are especially rich in tyrosine and phenylalanine—have a stimulating, protective, and regenerative effect on the skin.

The skin is stimulated through the metabolism taking place with the involvement of AMPc, which is activated by peptides and xanthine. The peptide derivatives, especially MAPX®, stimulate melanin synthesis. The semisynthetic peptides regenerate the connective tissue.

The protective and regenerative effect consists first of the light protective effect caused by newly formed melanin, which plays the role of a natural UV filter. It also consists of regeneration of UV-damaged cells by modulation of the cytokinins IL-1a and TNFα, as well as a synergistic effect of all the peptides present in the preparation with respect to free radicals. The anti-inflammatory effect (anti-IL-1a and anti TNFα) was determined experimentally as 55% or 40%.

The yeast extract used produces, among other things, a better structure of the skin cells and an improved moisture balance.

Dermatological testing of skin to which an advantageous composition of xanthine-associated peptides and semisynthetic marine peptides in combination with glucose polymers and marine mineral salts/trace elements had been applied showed an improvement in skin morphology to the extent that the keratin was very well hydrated, and there were far fewer vacuoles and less edema in comparison with untreated sections of skin. The dermis was well preserved and had normal connective tissue. The physical and chemical sunscreen filter content caused less skin irritation after being used for twenty-four hours.

The cosmetic preparation according to this invention can be used, for example, in sun creams, sun gels, after-sun products, day creams, night creams, masks, body lotions, cleansing milk, make-up, lipstick, body powder, eye cosmetics, hair masks, hair rinse, hair shampoo, shower gels, shower oils, bath oils. Such products are produced by methods with which those skilled in the art in this field are familiar.

This invention is described in greater detail below. The percentage amounts given in the examples are percent by weight (wt %).

BRIEF DESCRIPTION OF THE DRAWING

In the accompanying drawing.

DETAILED DESCRIPTION OF PREFERRED EMBODIMENT

Example 1

Figure 1:
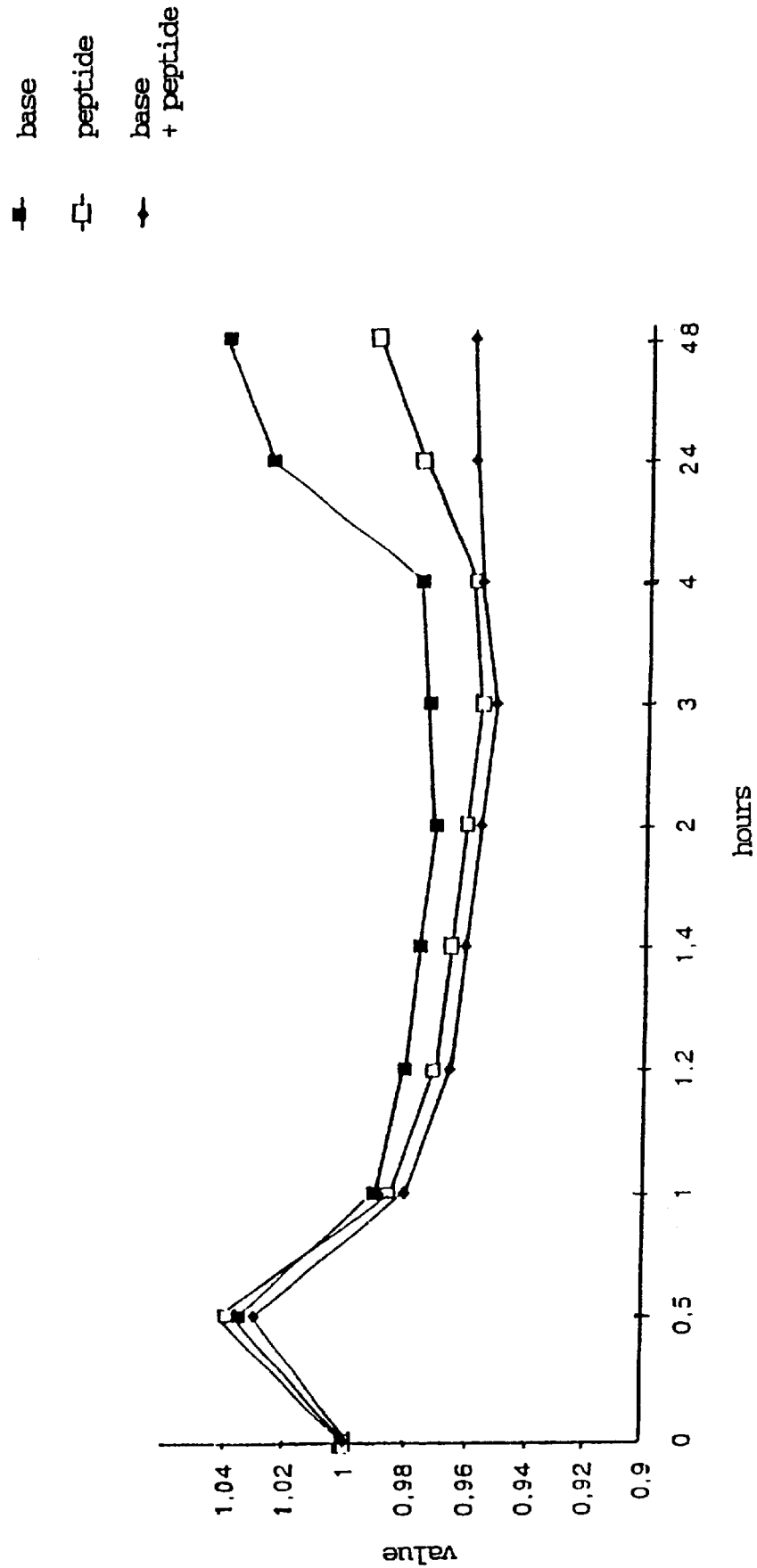
FIG. 1 shows a diagram of the Mexameter measurement of reddened skin with a comparison of various emulsions.

1A) Preparation of the yeast digestion product

A yeast suspension was prepared from yeast of the strain *Saccharomyces cerevisiae* enriched with peroxide dismutase and the following ingredients:

20% yeast
10% propylene glycol
0.4% preservative
water to 100%.

The ingredients were mixed and cooled to about 8 to 10° C. The yeast suspension was treated according to Example 1 of German Patent No. 4,241,154 C1, with approximately three liters of digestion product being removed per hour from the flow-through cell at a maximum temperature of 20° C. After separating the cell walls, a product with the following active ingredient contents is obtained:

| peroxide dismutase | ≧200 U/mL | |
|---|---|---|
| protease | ~50 U/mL | (U = units) |
| vitamin $B_2$ | 20 mg/L | |
| vitamin E | 0.6 mg/mL | |
| vitamin $B_6$ | 40 mg/L | |
| vitamin $B_{12}$ | 3 mg/L | |
| vitamin $D_2$ | 0.3 mg/mL | |

1B) Preparation of the cosmetic emulsion

The following examples were conducted with the yeast digestion product according to Example 1A and with the following general procedure in Examples 2–4.

Phase B, heated to about 80° C., was added to phase A at approximately 80° C. while stirring. The mixture was homogenized, cooled and mixed with phase C at about 35° C. The mixture was homogenized.

Example 2 Sun Cream

Preparation according to Example 1B

| Phase A | |
| --- | --- |
| glycerin | 3.0% |
| magnesium sulfate | 0.5% |
| water | to 100% |
| Phase B | |
| glyceryl oleate | 2.5% |
| decyl oleate | 5.0% |
| paraffin oil | 10.0% |
| beeswax | 2.0% |
| TiO₂ | 3.0% |
| zinc stearate | 2.0% |
| Phase C | |
| preservative | 0.3% |
| perfume oil | 0.5% |
| peptide preparation MAP-X ® | 1.0% |
| yeast digestion product according | to 0.5% |

Example 3 After-sun Preparation

Product prepared according to Example 1B

| Phase A | |
| --- | --- |
| Glycerin | 6.0% |
| Magnesium sulfate | 1.0% |
| Water | to 100% |
| Phase B | |
| Glyceryl oleate | 4.0% |
| Polyglyceryl-3 diisostearate | 10.0% |
| Hexyldecanol | 2.0% |
| Beeswax | 1.0% |
| Dicapryl ether | 2.0% |
| Phase C | |
| Preservative | 0.4% |
| Perfume oil | 0.5% |
| Peptide preparation MAP-X ® | 2.0% |
| Yeast digestion product according | to 5.0% |

Example 4 Body Lotion

Lotion prepared as in Example 1B

| Phase A | |
| --- | --- |
| Glycerin | 3.0% |
| Magnesium sulfate | 0.5% |
| Propylene glycol | 2.0% |
| Water | to 100% |
| Phase B | |
| Glyceryl oleate | 1.0% |
| Polyglyceryl-2 dipolyhydroxystearate | 2.5% |
| Cetearyl ionanoate | 3.0% |
| Jojoba oil | 1.5% |
| Phase C | |
| Preservative | 0.4% |

| | |
| --- | --- |
| Perfume oil | 1.5% |
| Peptide preparation MAP-X ® | 3.0% |
| Yeast digestion product according | to 8.0% |

Example 5 Lipstick

Phase A was melted at about 85° C. Phase B was stirred well with the color, and phase A was added. Then phase C was added and stirred, and the mixture was cooled.

| Phase A | |
| --- | --- |
| Candelilla wax (vegetable wax) | 8.0% |
| Beeswax | to 100% |
| Phase B | |
| Ceraphyl oil | 25.0% |
| Calendula oil | 25.0% |
| Pigment (depending on color) | 8.0% |
| Phase C | |
| Peptide preparation MAP-X ® | 2.0% |
| Yeast digestion product according | to 2.0% |
| Fragrance | 1.0% |

Example 6 Shower Gel

Water was placed in the vessel first, and then the following ingredients were added in the usual manner while stirring and then homogenizing.

| | |
| --- | --- |
| Water | to 100% |
| Disodium myreth sulfate | 25% |
| Disodium laureth sulfosuccinate | 8% |
| Preservative | 0.2% |
| Pefume oil | 0.5% |
| Peptide preparation MAP-X ® | 0.5% |
| Yeast digestion product according | to 0.1% |

Example 7

FIG. 1 shows a comparison of different emulsions in measurement of the reddening of the skin of volunteers. The values are the averages of ten measurements. The initial value 1 was arbitrarily set as a dimensionless proportionality factor (index). The measurements are performed at the times indicated in the curves. The measurements were made using a Mexameter® MX16 from the company Courage+Khazaka Electronic GmbH, Germany. Absorption of wavelengths 568 and 660 nm is measured here, with one wavelength corresponding approximately to the absorption peaks of hemoglobin in the skin, and the other wavelength preferably excluding other color influences (e.g., bilirubin) as much as possible. The measured values thus obtained are given as the proportionality factor (index) of the colors used.

The following were compared:
- A a base emulsion containing only the emulsion base and 0.5 wt % of the yeast digestion product according to Example 1A ("base")
- B peptide preparation MAP-X® in a concentration of 50 mg pure peptide per kg ("peptide")
- C same base emulsion as in A with 0.5% peptide preparation MAP-X® ("peptide+base").

The shape of the curve after 24 hours and 48 hours shows clearly that emulsion C has an unexpected improvement in relation to A or B.

Since the effect of antioxidants must be evaluated in the manner of complex physiological control circuits in a biological system, a simple additive effect of the two substances with the given antioxidant effect is not observed. Instead, an overall effect only slightly higher than the normal value is to be expected. Thus the difference in measurement results must clearly be regarded as a synergistic effect.

Example 8 24-hour Skin Protection Cream (Before-sun and After-sun Protection)

| Phase A | |
| --- | --- |
| C12-15 alkylbenzoate | 4.0% |
| Shea butter | 2.0% |
| Steareth-2 | 1.5% |
| Phase B | |
| Distilled water | to 100% |
| Cross polymer | 0.5% |
| Glycerin | 2% |
| Phase C | |
| Triethanolamine | 0.5% |
| Phase D | |
| Jojoba oil | 2% |
| olive oil | 1% |
| Preservative | 0.5% |
| Phase E | |
| Sun Marine Complex | 5.0% |
| Yeast digestion product according to | 0.5% |
| Perfume oil | 0.2% |

The cream was prepared by stirring the ingredients of phases A and B separately at about 60° C., then mixing the two phases together at this temperature, and finally cooling to about 45° C. Next, phases C and D were added and the mixture was cooled while stirring. Phase E was added at 35° C. and stirred with the overall mixture.

Example 9 Sun Cream (SPF 10)

| Phase A | |
| --- | --- |
| Steareth-2 | 3% |
| Steareth-21 | 2% |
| Beeswax | 1.5% |
| Phase B | |
| Distilled water | to 100% |
| Glycerin | 3.5% |
| Propylene glycol | 2.0% |
| $TiO_2$ | 7.0% |
| Phase C | |
| Jojoba oil | 2.5% |
| Babassu oil | 1.0% |
| Silicone oil | 0.5% |
| Preservative | 0.3% |
| Phase D | |
| Sun Marine Complex | 0.5% |
| Yeast digestion product according to | 0.5% |
| Perfume oil | 0.1% |

It is prepared as described in Example 8.

Example 10 Sun Cream (SPF 15)

| Phase A | |
| --- | --- |
| Steareth-2 | 2.0% |
| Steareth-21 | 2.0% |
| Isohexadecane | 3.0% |
| Octyl methoxycinnamate | 5.0% |
| 4-methylbenzylidene camphor | 3.3% |
| Phase B | |
| Distilled water | to 100% |
| Glycerin | 10.0% |
| $TiO_2/SiO_2$ agglomerate* | 2.0% |
| $ZnO/SiO_2$ agglomerate* | 1.0% |
| Phase C | |
| Silicone oil | 2.0% |
| Palm oil | 4.0% |
| Preservative | 0.3% |
| Phase D | |
| Sun Marine Complex | 0.5% |
| Yeast digestion product according to | 0.5% |
| Perfume oil | 0.2% |

*from spherical nonporous $SiO_2$ particles of 0.05–1.5 µm and spherical $TiO_2$ and ZnO particles, where the agglomerates have a particle size of 0.06–1.5 µm.

The preparation was processed according to Example 8.

Example 11 Sun Cream with Chemical Filters

| Phase A | |
| --- | --- |
| Cetearyl | 1.5% |
| Glyceryl steareth, ceterareth 20, cetyl | 3.5% |
| Octyl steareth | 1.5% |
| OctYl methoxycinnamate | 6.5% |
| 4-Methylbenzylidene camphor | 1.5% |
| Phase B | |
| Distilled water | to 100% |
| Glycerin | 2.0% |
| Phase C | |
| Babassu oil | 5.0% |
| Preservative | 0.5% |
| Phase D | |
| Sun Marine Complex | 3.0% |
| Yeast digestion product according to | 0.5% |
| Perfume oil | 0.1% |

Cream processed according to Example 8.

Example 12 Make-up with SPF 4

| Phase A | |
| --- | --- |
| Shea butter | 2% |
| Beeswax | 3% |
| olive oil | 5% |
| Color | 3–10% |
| $TiO_2$ | 4% |
| Phase B | |
| Distilled water | to 100% |
| Glycerin | 2% |

-continued

| Phase C | |
|---|---|
| Jojoba oil | 2% |
| Silicone oil | 5% |

The composition was processed according to Example 8.

What is claimed is:

1. A cosmetic preparation with a peptide additive, comprising as active ingredients a combination of the following ingredients:
    a) a peptide derivative of the formula (Lip)X-His-Phe-Arg-Y, where
        Lip represents thioctic acid or one of its derivatives,
        X denotes Glu, OH, or $NH_2$
        Y denotes Trp-Gly-OH, Trp-Gly-$NH_2$, Trp-$NH_2$ or
        Phe denotes Homo-Phe or P-fluoro-Phe,
    and the amino acids may be present in the form D, L or DL, or mixtures thereof, in the amount of 0.05 to 2.5 mg pure peptide derivative per kg total weight, where the peptide derivative is mixed with xanthine in a ratio of 0.5 to 2 mol per 100 mol peptide;
    b) at least 0.5 wt % of a mixture of enzymes and vitamins containing at least 150 U/mL peroxide dismutase (POD);
    c) 65 to 99.5 wt % of an inert, non-toxic cosmetically acceptable carrier; and
    d) 0 to 12 wt % other active ingredients, where the percentage amounts are all based on the total weight of the preparation.

2. A preparation according to claim 1,
    wherein the mixture of enzymes and vitamins, of (b) are peroxide dismutase, protease, vitamin B2, vitamin B6, vitamin B12, and vitamin E.

3. A preparation according to claim 1,
    wherein it contains protease and vitamins B and D, with the ratio of peroxide dismutase to protease, expressed as international units, being in the range of 3:1 to 8:1.

4. A preparation according to claim 2,
    wherein the mixture of enzymes and vitamins of (b) originates from ultrasonic digestion of a yeast.

5. A preparation according to claim 1,
    wherein the peptide derivative of (a) is selected from the group consisting of I ((DL)Lip)-Glu-His-D.HomoPhe-Arg-Trp-Gly-$NH_2$
    II ((DH)Lip)-Glu-His-D.HomoPhe-Arg-Trp-Gly-$NH_2$
    III ((DL)Lip)-Glu-His-para-fluoro-Phe-Arg-Trp-Gly-$NH_2$
    IV ((DH)(Lip)-His-D.HomoPhe-Arg-Trp-Gly-$NH_2$
    V (N.Lipoyl-lysine)-Glu-His-D.HomoPhe-Arg-Trp-Gly-$NH_2$
    VI (N.Lipoyl-lysine)-His-D.HomoPhe-Arg-Trp-Gly-$NH_2$
    VII (N.Lipoyl-lysine)-His-D.HomoPhe-Arg-Trp-$NH_2$
    and as well as derivatives of these molecules in a form of salts of esters or amides.

6. A preparation according to claim 1, wherein the peptide component is present in the amount of 0.05 to 1.5 mg pure peptide derivative per kg total weight.

7. A preparation according to claim 1,
    wherein the peptide derivative mixed with xanthine is present in the form of a mixture of peptide derivatives of the formula (Lip)X-His-Phe-Arg-Y and marine peptides and polypeptides, which are a protein fraction produced from micro-algae of the genus Chlorella and macroalgae of the genus Ulva mixed with byssus (mollusk silk), then mixed with a vegetable glucose polymer, and wherein marine peptides are mixed with 0.5 to 5 wt % marine mineral salts and trace elements.

8. A preparation according to claim 7,
    wherein it is a mixture of water, dextrin glycoproteins together with a mixture of Ulva and Chlorella algae extract and mollusk silk.

9. A cosmetic preparation with a peptide additive according to claim 1
    wherein the inert, non-toxic cosmetically acceptable carrier of (c) is selected from the group consisting of sun cream, sun emulsion, after-sun lotion, before-sun lotion, body lotion, lipstick, make-up, eye cosmetic, face powder, hair mask, hair shampoo, hair lotion, shower gel and shower oil.

10. A preparation according to claim 4,
    wherein the mixture of enzymes and vitamins of (b) originate from ultrasonic digestion of baker's yeast.

* * * * *